(12) United States Patent  
Menefield

(10) Patent No.: US 7,147,129 B1
(45) Date of Patent: Dec. 12, 2006

(54) PERSONAL EFFECTS DISPENSER

(76) Inventor: Mary Jane Menefield, 2032 Emine Dr., Tallahassee, FL (US) 32308

( * ) Notice: Subject to any disclaimer, the term of this patent is extended or adjusted under 35 U.S.C. 154(b) by 407 days.

(21) Appl. No.: 10/770,559

(22) Filed: Feb. 4, 2004

Related U.S. Application Data

(60) Provisional application No. 60/456,850, filed on Mar. 21, 2003.

(51) Int. Cl.
B65H 1/00 (2006.01)
B65G 59/00 (2006.01)
A61B 19/08 (2006.01)
B65D 73/00 (2006.01)
B65D 85/14 (2006.01)
A45D 27/22 (2006.01)

(52) U.S. Cl. ............... 221/283; 221/151; 221/123; 206/440; 206/494; 206/581; 206/69; 206/806; 132/315

(58) Field of Classification Search ............... 206/440, 206/494, 581, 233, 806, 813, 823, 69; 221/151, 221/92, 123, 282, 283, 287, 306; 132/314, 132/315; 248/339–341, 213.2, 222.41, 295.11
See application file for complete search history.

(56) References Cited

U.S. PATENT DOCUMENTS 2,902,187 A * 9/1959 Cabanban ............... 221/240
4,735,342 A * 4/1988 Goldstein ............... 221/25
5,857,586 A * 1/1999 Scherr ............... 221/45
6,439,386 B1* 8/2002 Sauer et al. ............... 206/494
6,520,376 B1* 2/2003 Verdone ............... 221/208
6,588,626 B1* 7/2003 Sauer et al. ............... 221/49
6,662,967 B1* 12/2003 Roy ............... 221/58
6,702,147 B1* 3/2004 Ashford ............... 221/34
6,799,695 B1* 10/2004 Borrero ............... 221/59

* cited by examiner

Primary Examiner—Mickey Yu
Assistant Examiner—J. Gregory Pickett
(74) Attorney, Agent, or Firm—Peter Loffler

(57) ABSTRACT

A dispenser dispenses personal effects such as, panty liners, condoms, wet wipes, tampons, etc., for use by occupants of a particular establishment (home, prison, office, hospital etc.). The personal effects dispenser has a first housing that holds the tampons and the panty liners and dispenses each within a respective opening on the housing with the opening for dispensing the tampons having a hinged door covering the opening. A second housing holds the condoms or wet wipes and has an opening that corresponds to an opening on the first housing whenever the second housing is received within the first housing. A spacer is received within the first housing in order to replace the second housing whenever the second housing is not being used. Various attachment schemes are used to attach the personal effects dispenser to a wall.

4 Claims, 4 Drawing Sheets

PERSONAL EFFECTS DISPENSER

This application claims the benefit of U.S. provisional patent application No. 60/456,850, filed on Mar. 21, 2003.

BACKGROUND OF THE INVENTION

1. Field of the Invention

The present invention relates to a personal effects dispenser that dispenses panty liners, tampons, wet wipes, condoms, etc., all within an aesthetic housing.

2. Background of the Prior Art

As sure as a guest room is prepared, guests are sure to follow. Household guests, whether family or friends, are a part of many people's lives, especially at critical times such as holidays, weddings, etc. In order to save money on hotel rooms, or just to further familial or fraternal bonding, guests stay with a receptive host. Most hosts tend to be as accommodating to their guests as possible. In many households, guests have their own bathrooms for upkeep of their personal hygiene. In attempting to accommodate the needs of the guests, the hosts stock the bathroom with the basic needs of the guests, such as shampoo, towels, soap, conditioner, basic medicine, etc. Additionally, many hosts accommodate the very intimately personal needs of the guests by providing items such as panty liners, tampons, and condoms among other items.

Many hosts place such personal items into a drawer or cabinet within the bathroom for retrieval of the item by the guest as needed. While efficient, this distribution system is not without flaws, as many guests are very reluctant to go through the drawers and cabinets of the hosts' bathroom. To address this problem, many hosts simply leave the personal items out in the open within the guest bathroom so that the guest can see the item in plain site and retrieve a particular item as needed. While practical, this system of personal item distribution makes many guests as well as some hosts somewhat uncomfortable. Such guests and hosts, believe, that while such personal items are a fact of life, they need not be in open display.

Accordingly, there exists a need in the art for a distribution system that allows a host to accommodate the needs of his or her guest by providing a means whereby the host can provide the guests with items of a personal nature, such as tampons, condoms, and panty liners, whereby the items are stored within an attractive and efficient housing which housing stores the personal items in a relatively discrete fashion while allowing the guest to be able quickly ascertain the nature of the items that are being dispensed by the housing. Such a distribution system must be of relatively simple and straightforward design and construction so as to be relatively inexpensive to manufacture so as to appeal to a relatively wide sector of the buying public. Such a distribution system must be relatively versatile in operation and must be easy to use, stock and otherwise maintain. The distribution system must be able to be mounted in a variety of settings within the host's household and must also work in other appropriate settings such as a female prison, church, offices, medical centers, hotel bathrooms, etc., for the convenience of the user of the particular establishment.

SUMMARY OF THE INVENTION

The personal effects dispenser of the present invention addresses the aforementioned needs in the art. The personal effects dispenser provides a personal effects distribution system that allows a host to accommodate the needs of his or her guest by providing a means whereby the host can provide the guests with items of a personal nature, such as tampons, condoms, and panty liners, etc. The personal effects dispenser provides an attractive and efficient housing which housing stores the various personal items desired by a guest in a relatively discrete fashion and allows the guest to be able quickly ascertain the nature of the items that are being dispensed by the personal effects dispenser. The personal effects dispenser is of relatively simple and straightforward design and construction and is relatively inexpensive to manufacture and thereby appeals to a relatively wide sector of the buying public. The personal effects dispenser is relatively versatile in operation and is easy to use, stock and otherwise maintain. The personal effects dispenser is capable of being mounted in a variety of settings within the host's household and can be color coordinated as a buyer sees fit. The present invention can also be used in other settings such as churches, hospitals, schools, prisons, especially female prisons, offices, etc.

The personal effects dispenser of the present invention is comprised of a first housing that has a bottom, an open top, a front surface, a back surface, a first opening located on the front surface, a second opening located on the front surface, and a third opening located on the front surface such that a first item (such as a panty liner or pad) is dispensed through the first opening, a second item (such as a condom or a wet wipe) is dispensed through the second opening, and a third item (such as a tampon) is dispensed through the third opening. A lid is hingedly attached to the first housing for covering the open top. A mounting means is provided for mounting the first housing onto a vertical surface, such as a wall. The mounting means may comprise an adhesive material attached to the back surface of the first housing which adhesive material adheres to the vertical surface. The mounting means may also comprise a key hole slot that is located on the back surface of the first housing. A hook and a collar that receives the hook are provided, such that a set screw passes through the collar and engages the hook for holding the hook secure within the collar, with the set screw also being received within the key hole slot located in the housing. A spacer may be provided and may be removably received within the first housing for blocking the opening of the second opening. A second housing that has a fourth opening may be provided such that the second housing is removably received within the first housing and such the second housing holds the second item and that when the second housing is received within the first housing the fourth opening aligns with the second opening. A door may be hingedly attached to the first housing such that the door provides and retards access to the third opening.

BRIEF DESCRIPTION OF THE DRAWINGS

Similar reference numerals refer to similar parts throughout the several views of the drawings.

DESCRIPTION OF THE PREFERRED EMBODIMENT

Figure 1:
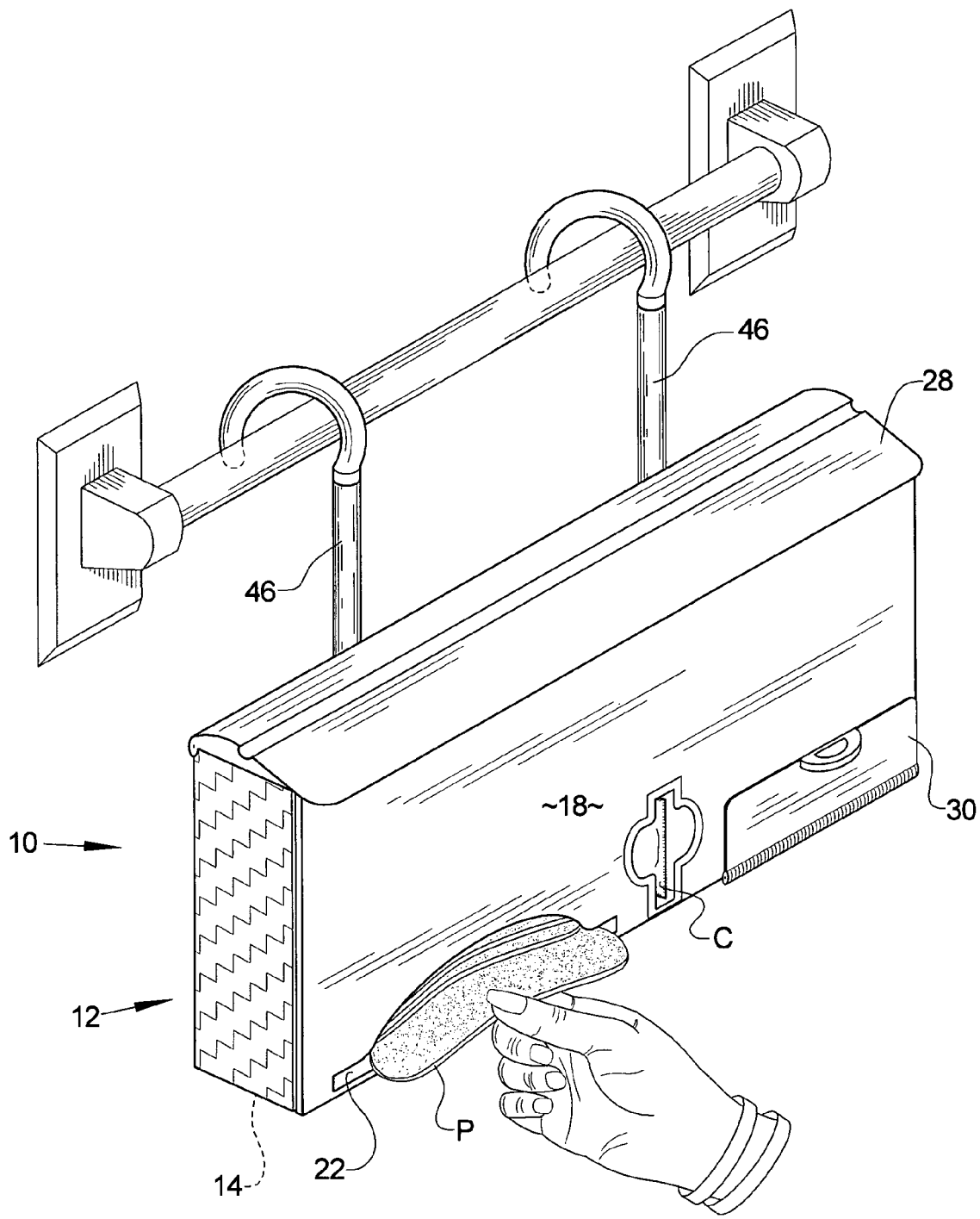
FIG. 1 is a perspective view of the personal effects dispenser of the present invention dispensing a panty liner.
Figure 2:
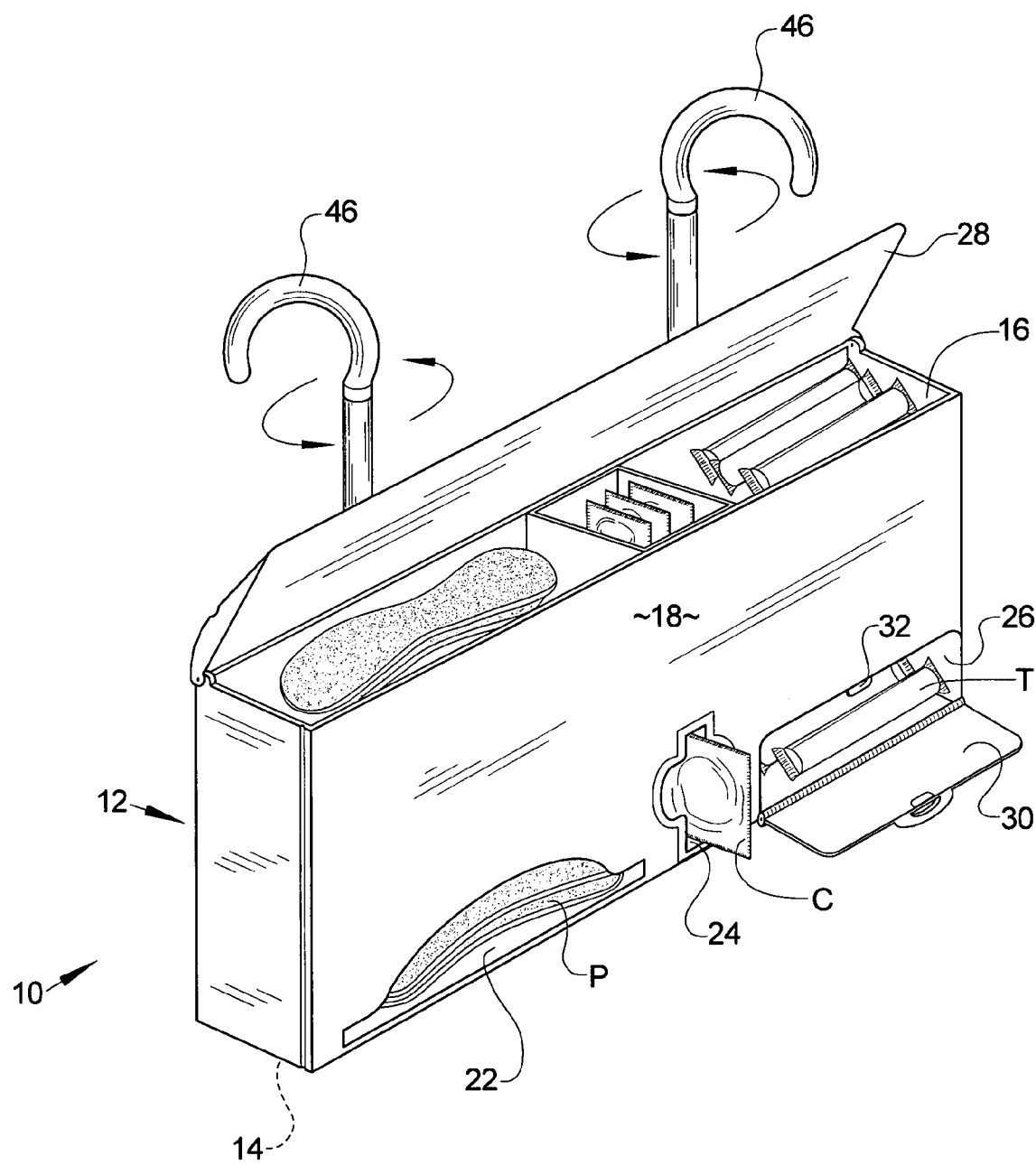
FIG. 2 is a perspective view of the personal effects dispenser with all compartments loaded and ready to dispense.
Figure 3:
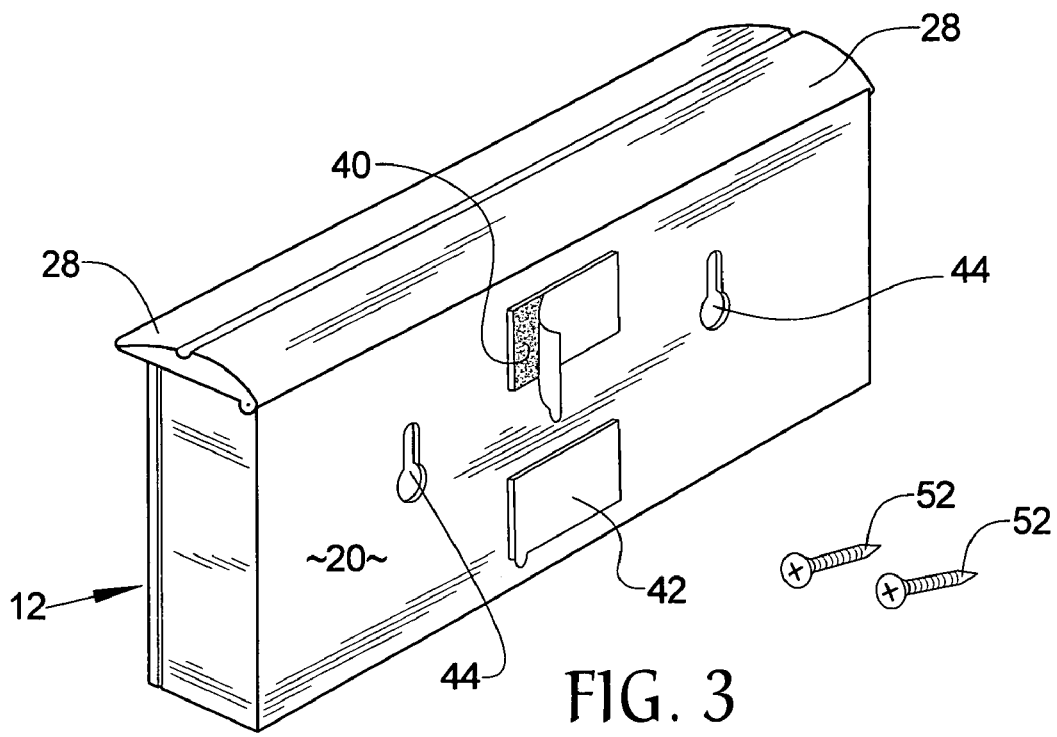
FIG. 3 is a rear perspective view of the personal effects dispenser illustrating a mounting method for the dispenser.
Figure 4:
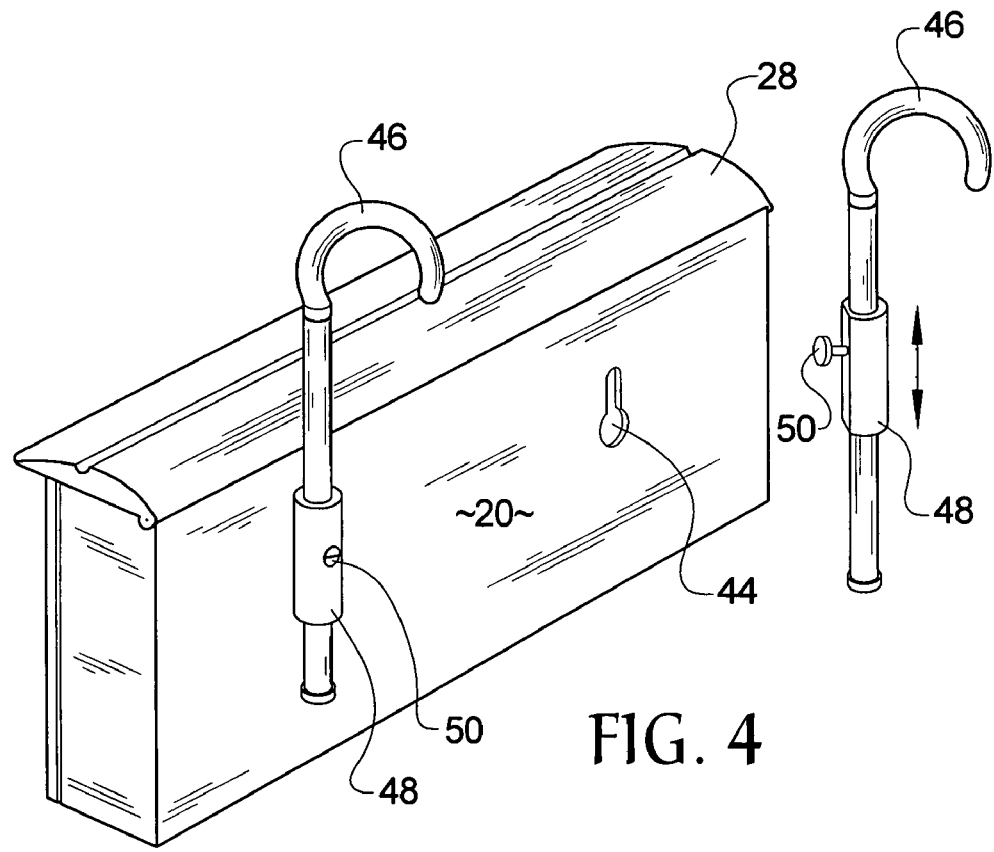
FIG. 4 is a rear perspective view of the personal effects dispenser illustrating an alternate mounting method for the dispenser.
Figure 5:
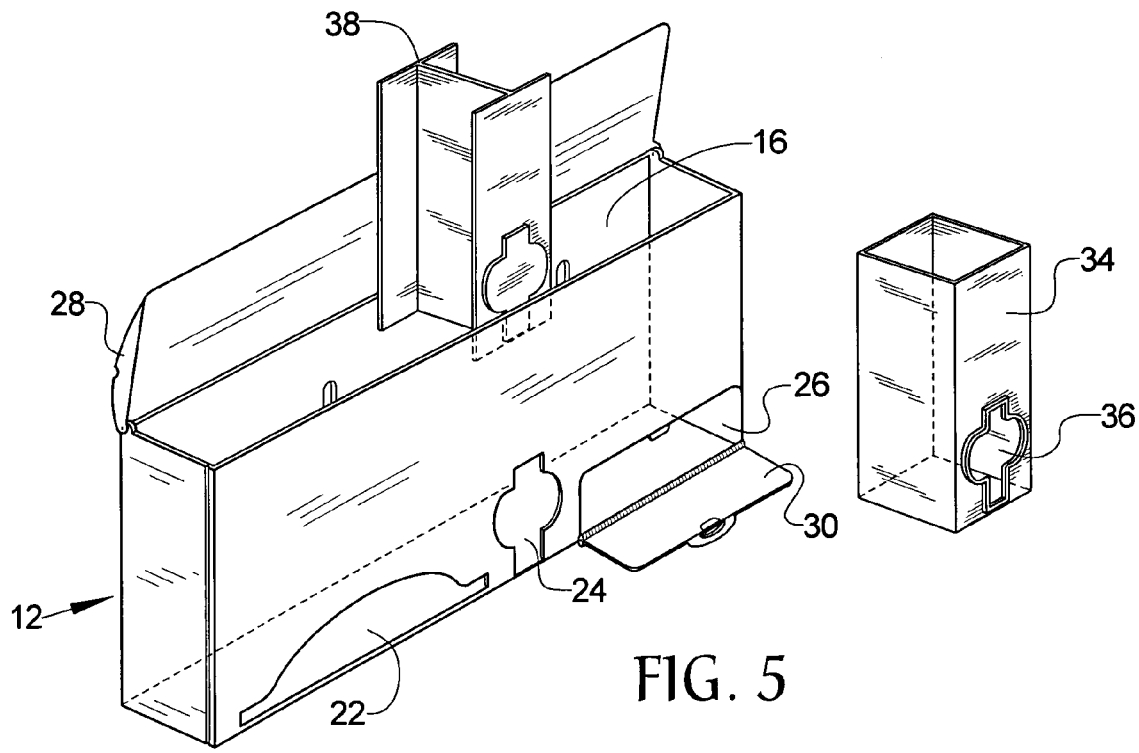
FIGS. 5 and 6 are perspective views illustrating the condom dispenser being replaced by a spacer for non-condom use of the personal effects dispenser.
Figure 6:
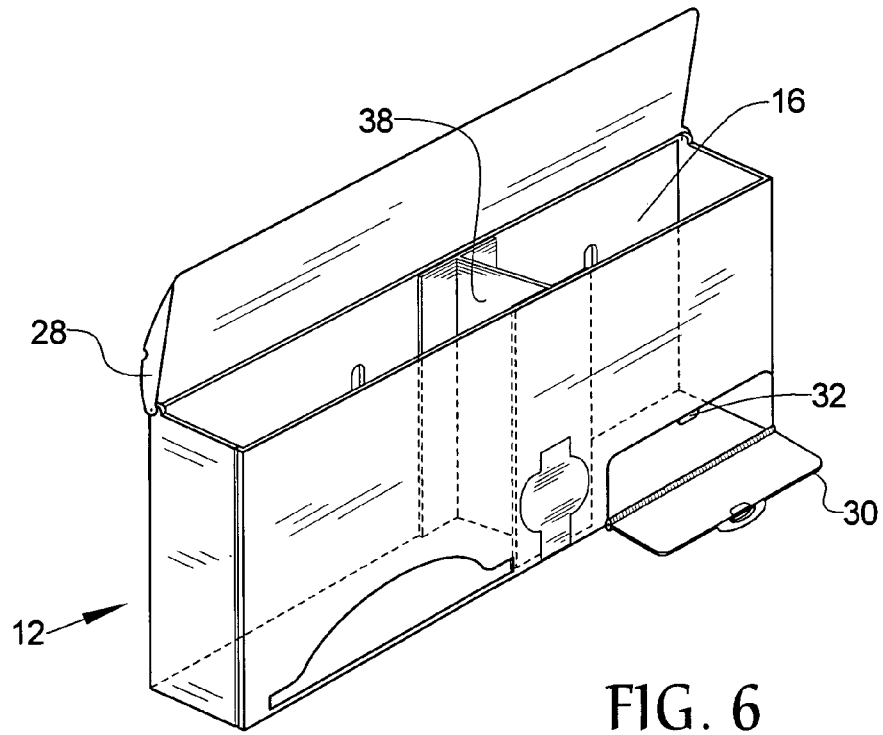

Referring now to the drawings, it is seen that the personal effects dispenser of the present invention, generally denoted by reference numeral 10, is comprised of a first housing 12 that has a bottom 14, which may have one or more openings (none illustrated (to dispel any accumulated fluid therein, an open top 16, a front surface 18, a back surface 20, a first opening 22 located on the front surface 18, a second opening 24 located on the front surface 18, and a third opening 26 located on the front surface 18. A top 28 is hingedly attached to the first housing 12 in order to close the open top 16 of the first housing 12 and to provide restocking access to the first housing 12 therethrough. The outer surface of the first housing 12 as well as the outer surface of the top 28 may have appropriate texturing thereon in order to provide an aesthetic appearance to the personal effects dispenser 10.

A first item P (such as a panty liner) is dispensed through the first opening 22, a second item C (such as a condom or wet wipe) is dispensed through the second opening 24, and a third item T (such as a tampon) is dispensed through the third opening 26. A door 30 is hingedly attached to the housing 12 in order to provide doored access to the third opening 26. An appropriate latch 32, such as the illustrated magnetic latch, may be used to hold the door 30 in the closed position with respect to the third opening 26. The condom C or wet wipe may be held within a second housing 34 that is removably received within the first housing 12 such that the second housing 34 has a fourth opening 36 that aligns with the second opening 24 of the first housing 12 such that whenever the second housing 34, which holds the condoms C to be dispensed, is received within the first housing 12, the fourth opening 36 aligns with the second opening 24 and the condoms C or wet wipes are dispensed through the aligned second opening 24 and fourth opening 36.

A spacer 38 may be provided and may be removably received within the first housing 12 such that the spacer 38 is placed into the first housing 12 whenever the second housing 34 is removed from the first housing 12. For example, if the personal effects dispenser 10 is being used with a predominantly female population, and the need for dispensing condoms C is small, the second housing 34 holding the condoms C to be dispensed, may be removed from the first housing 12 and replaced by the spacer 38 which covers up the second opening 24 that normally dispenses condoms C therethrough.

An appropriate mounting means is provided for mounting the first housing 12 onto a vertical surface, such as a wall. The mounting means may comprise an adhesive material 40, which may be covered by an appropriate liner 42, attached to the back surface 20 of the first housing 12 which adhesive material adheres to the vertical surface. In use, the adhesive material 40 is secured to the back surface 20 of the first housing 12 and the protective liner 42 is removed and the first housing 12 is adhered to an appropriate surface, such as a wall, via the adhesive material 40. Alternately, the mounting means may comprise a key hole slot 44 that is located on the back surface 20 of the first housing 12. A hook 46 and a collar 48 that receives the hook 46 are provided, such that a set screw 50 passes through the collar 48 and engages the hook 46 for holding the hook 46 secure within the collar 48, with the set screw 50 also being received within the key hole slot 44 located in the first housing in standard fashion. The hook 46 may swivel within the collar 48 as needed. Alternately, appropriate screws 52 may be positioned within the wall and received within the key hole slots 44 located on the back surface 20 first housing 12

In order to use the personal effects dispenser of the present invention, the first housing 12 is mounted onto an appropriate wall using a desired mounting system, or the first housing 12 may simply be set upon an appropriate surface such as a bathroom counter. The top 28 is opened in order to gain access to the interior of the first housing 12. Appropriate items such as panty liners P are stocked within the first housing 12 such that the panty liners P are dispensable through the first opening 22 located on the first housing 12. Similarly, items, such as tampons T are stocked within the first housing 12 such that the tampons T are dispensable through the third opening 26 located on the first housing 12. Condoms C or wet wipes are placed into the second housing 34 and the second housing 34 is placed into the first housing 12 such that the fourth opening 36 of the second housing 34 aligns with the second opening 24 of the first housing 12 in order to allow condoms C to be dispensed through the aligned second opening 24 and fourth opening 36. If condom C dispensing is not desired, the second housing 34 may be removed from the first housing 12 and be replaced with the spacer 38 which covers the second opening 24 of the first housing 12.

While the invention has been particularly shown and described with reference to an embodiment thereof, it will be appreciated by those skilled in the art that various changes in form and detail may be made without departing from the spirit and scope of the invention.

I claim:

1. A dispenser comprising:
   a first housing having a bottom, an open top, a front surface, a back surface, a first opening located on the front surface, a second opening located on the front surface, and a third opening located on the front surface such that a first item is dispensed through the first opening, a second item is dispensed through the second opening, and a third item is dispensed through the third opening;
   a lid, hingedly attached to the first housing for covering the open top, a key hole slot located on the back surface of the first housing;
   a hook;
   a collar that receives the hook; and
   a set screw that passes through the collar and engages the hook for holding the hook secure within the collar, the set screw also being received within the key hole slot.

2. The dispenser as in claim 1 further comprising a second housing that has a fourth opening, the second housing being removably received within the first housing such the second housing holds the second item and that when the second housing is received within the first housing the fourth opening aligns with the second opening.

3. The dispenser as in claim 1 further comprising a spacer that is removably received within the first housing for blocking the opening of the second opening.

4. The dispenser as in claim, 1 further comprising a door, hingedly attached to the first housing such that the door provides and retards access to the third opening.

* * * * *